United States Patent [19]

Van Gemert

[11] Patent Number: 5,645,767
[45] Date of Patent: Jul. 8, 1997

[54] PHOTOCHROMIC INDENO-FUSED NAPHTHOPYRANS

[75] Inventor: Barry Van Gemert, Murrysville, Pa.

[73] Assignee: Transitions Optical, Inc., Pinellas Park, Fla.

[21] Appl. No.: 542,993

[22] Filed: Oct. 13, 1995

Related U.S. Application Data

[63] Continuation-in-part of Ser. No. 333,701, Nov. 3, 1994, abandoned.

[51] Int. Cl.[6] .................. C08K 5/15; G02B 5/23; C07D 311/78; C07D 405/04
[52] U.S. Cl. .................. 252/586; 549/382; 549/362; 549/337; 549/60; 549/58; 548/526; 548/525; 548/518; 548/454; 546/197; 546/196; 546/194; 546/167; 546/280.7; 546/284.1; 546/281.1; 544/150; 544/148; 544/124; 524/110; 524/104; 524/99; 524/87
[58] Field of Search .................. 252/586; 524/110, 524/104, 99, 87; 544/150, 148, 124; 546/270, 269, 197, 196, 194, 167; 548/526, 525, 518, 454; 549/382, 362, 337, 60, 58

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/300 |
| 4,563,458 | 1/1986 | Widdig et al. | 252/586 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 4,931,221 | 6/1990 | Heller et al. | 252/586 |
| 5,066,818 | 11/1991 | Van Gemert | 549/389 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,369,158 | 11/1994 | Knowles | 524/110 |
| 5,384,077 | 1/1995 | Knowles | 252/586 |
| 5,395,567 | 3/1995 | Van Gemert et al. | 252/586 |
| 5,405,958 | 4/1995 | Van Gemert et al. | 252/586 |
| 5,429,774 | 7/1995 | Kumar | 252/586 |
| 5,451,344 | 9/1995 | Knowles et al. | 252/586 |
| 5,458,814 | 10/1995 | Kumar et al. | 252/586 |
| 5,466,398 | 11/1995 | Van Gemert et al. | 252/586 |
| 5,514,817 | 5/1996 | Knowles | 252/586 |

FOREIGN PATENT DOCUMENTS

| | | |
|---|---|---|
| 246114 | 5/1987 | European Pat. Off. . |
| 250193 | 6/1987 | European Pat. Off. . |
| 294056 | 12/1988 | European Pat. Off. . |
| 62-195383 | of 1987 | Japan . |
| 02/69471 | 3/1990 | Japan . |

OTHER PUBLICATIONS

*Friedel–Crafts and Related Reactions*, George A. Olah, Interscience Publishers, vol. 3, Chap. XXXI, pp. 1–8, 1964.
"Regioselective Friedel Crafts Acylation of 1,2,3,4–Tetrahydroquinoline and Related Nitrogen Heterocycles; Effects of NH Protective Groups and Ring Size", Ishihara, Y., et al, J. Chem. Soc., Perkin Trans. 1, pp. 3401–3406, 1992.
"1–Phenylnaphthalenes. part IV. The Cyclisation of Methyl Hydrogen cis and trans–γ–o–Methoxyphenyl– and Ethyl Hydrogen cis— and trans–γ–p–Methoxyphenyl–γ–phenylitaconate to the Corresponding 1–Phenylnaphthalenes", Baddar, F.G. et al., Journal of the Chemical Society, pp. 986–994, 1958.
"Behavior of α–Substituted Chalcones on Attempted Friedel–Crafts Arylation", Koelsch, C.F., The Journal of Organic Chemistry, vol. 26, pp. 2590–2592, 1961.
*The Chemistry of the Carbonyl Group*, Saul Patai, Editor, Interscience Publishers. Chapter 11, pp. 507–566, 1966.

*Primary Examiner*—Nicky Chan
*Attorney, Agent, or Firm*—Frank P. Mallak; Irwin M. Stein

[57] ABSTRACT

Described are novel photochromic indeno-fused naphthopyran compounds, examples of which are naphthopyran compounds having a substituted or unsubstituted indeno group, the 2,1 positions of which are fused to the f side of the naphtho portion of the naphthopyran, and certain substituents at the 3-position of the pyran ring. Certain substituents may also be present at the number 5, 6, 7, 8, 9, 10, 11, 12, or 13 carbon atoms of the compounds. These compounds may be represented by the following graphic formula:

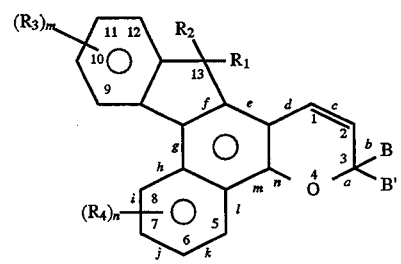

Also described are polymeric organic host materials that contain or that are coated with such compounds. Optically clear articles such as ophthalmic lenses or other plastic transparencies that incorporate the novel naphthopyran compounds or combinations thereof with complementary photochromic compounds, e.g., certain other naphthopyrans, benzopyrans, and spiro(indoline)type compounds, are also described.

22 Claims, No Drawings

PHOTOCHROMIC INDENO-FUSED NAPHTHOPYRANS

CROSS-REFERENCE TO RELATED APPLICATION

This application is a continuation-in-part of application Ser. No. 08/333,701, filed Nov. 3, 1994, now abandoned.

DESCRIPTION OF THE INVENTION

The present invention relates to certain novel naphthopyran compounds. More particularly, this invention relates to novel photochromic indeno-fused naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions.

The present invention relates to novel substituted naphthopyran compounds having a substituted or unsubstituted indeno group, the 2,1 positions of which are fused to the f side of the naphtho portion of the naphthopyran, and certain substituents at the 3-position of the pyran ring. These compounds have unexpectedly been found to demonstrate a bathochromic shift for the wavelength in the visible spectrum at which the maximum absorption of the activated (colored) form of the photochromic compound, i.e., the lambda max (Vis), occurs, thereby resulting in activated colors ranging from orange to blue/gray. In addition, these compounds have demonstrated a high molar absorptivity (or molar extinction coefficient) in the UV, an acceptable fade rate without the addition of acids or bases, a high activated intensity, and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel indeno[2,1-f]naphtho[1,2-b] pyrans having activated colors ranging from orange to blue/gray, an acceptable fade rate, high activated intensity and a high coloration rate may be prepared. These compounds may be described as indeno fused [1,2-b m] naphthopyrans having certain substituents at the 3 position of the pyran ring. Certain substituents may also be present at the number 5, 6, 7, 8, 9, 10, 11, 12, or 13 carbon atoms of the compounds. These compounds may be represented by the following graphic formula in which the letters a through n represent the sides of the naphthopyran rings, and the numbers represent the numbers of the ring atoms of the naphthopyran:

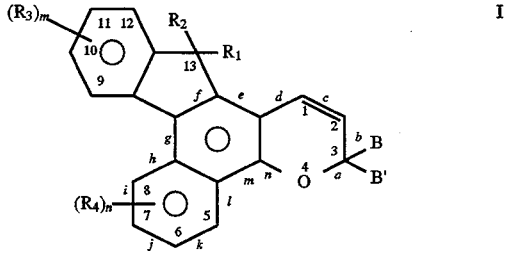

In graphic formula I, $R_1$ and $R_2$ may together form an oxo group, a spiro-heterocyclic group containing 2 oxygen atoms and 3 to 6 carbon atoms including the spirocarbon atom, which may be represented by the expression (—O—($C_2$–$C_5$ alkanediyl)—O—), e.g., spiro-1,3-dioxolane-2, spiro-1,3-dioxane-2, etc. or $R_1$ and $R_2$ may each be hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group —C(O)W, wherein W is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$)alkylamino, e.g. dimethyl amino, methyl propyl amino, etc., or $R_1$ and $R_2$ may each be the group, —$OR_5$, wherein $R_5$ is $C_1$–$C_6$ alkyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_6$)X, wherein $R_6$ is hydrogen or $C_1$–$C_3$ alkyl and X is CN, $CF_3$, or $COOR_7$, and $R_7$ is hydrogen or $C_1$–$C_3$ alkyl, or $R_5$ is the group, —C(O)Y, wherein Y is hydrogen, $C_1$–$C_6$ alkyl, $C_1$–$C_6$ alkoxy, the unsubstituted, mono- or di-substituted aryl groups, phenyl or naphthyl, phenoxy, mono- or di-($C_1$–$C_6$)alkyl substituted phenoxy, mono- or di-($C_1$–$C_6$)alkoxy substituted phenoxy, amino, mono($C_1$–$C_6$)alkylamino, di($C_1$–$C_6$)alkylamino, phenylamino, mono- or di-($C_1$–$C_6$)alkyl substituted phenylamino, or mono- or di-($C_1$–$C_6$)alkoxy substituted phenylamino, each of the aforedescribed phenyl, benzyl and aryl group substituents being $C_1$–$C_6$ alkyl or $C_1$–$C_6$ alkoxy.

More preferably, $R_1$ and $R_2$ are each selected from the group consisting of hydrogen, hydroxy, $C_1$–$C_4$ alkyl, $C_3$–$C_6$ cycloalkyl, chloro, fluoro and the group, —$OR_5$, wherein $R_5$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$)alkyl, $C_1$–$C_3$ chloroalkyl, $C_1$–$C_3$ fluoroalkyl, the group, —$CH(R_6)$X, wherein $R_6$ is hydrogen or $C_1$–$C_2$ alkyl and X is CN or $COOR_7$, $R_7$ being hydrogen or $C_1$–$C_2$ alkyl, or $R_5$ is the group, —$C(O)Y$, wherein Y is hydrogen, $C_1$–$C_3$ alkyl, $C_1$–$C_3$ alkoxy, phenyl, naphthyl, the mono-substituted aryl groups, phenyl or naphthyl, phenoxy, mono- or di-($C_1$–$C_3$) alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, each of said aryl group substituents being $C_1$–$C_3$ alkyl or $C_1$–$C_3$ alkoxy. Most preferably, $R_1$ and $R_2$ are each hydrogen, hydroxy, $C_1$–$C_4$ alkyl or the group, —$OR_5$, wherein $R_5$ is $C_1$–$C_3$ alkyl.

$R_3$ and $R_4$ in graphic formula I may each be $C_1$–$C_6$ alkyl, $C_1$–$C_6$ alkoxy, chloro or fluoro; m and n are each the integers 0, 1, or 2; $R_3$ may be located at the number 10 and/or number 11 ring atoms of the naphthopyran; and $R_4$ may be located at the number 6 and/or number 7 ring atoms. When m and n are 2, the $R_3$ (and $R_4$) substituents may be the same or different. More preferably, $R_3$ and $R_4$ are each $C_1$–$C_3$ alkyl, $C_1$–$C_3$ alkoxy, or fluoro; m and n are each the integers 0 or 1; $R_3$ is located at the number 11 ring atom; and $R_4$ is located at the number 6 ring atom. Most preferably, $R_3$ and $R_4$ are each $C_1$–$C_3$ alkyl or $C_1$–$C_3$ alkoxy, and m and n are each the integers 0 or 1.

B and B' in graphic formula I may each be selected from the group consisting of: (i) the unsubstituted, mono-, di-, and tri-substituted aryl groups, phenyl and naphthyl; (ii) the unsubstituted, mono- and di-substituted aromatic heterocyclic groups pyridyl, furanyl, benzofuran-2-yl, benzofuran-3-yl, thienyl, benzothien-2-yl, benzothien-3-yl, each of said aryl and aromatic heterocyclic substituents in parts (i) and (ii) being selected from the group consisting of hydroxy, amino, mono($C_1$–$C_6$)alkylamino, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, chloro and fluoro; (iii) the groups represented by the following graphic formulae:

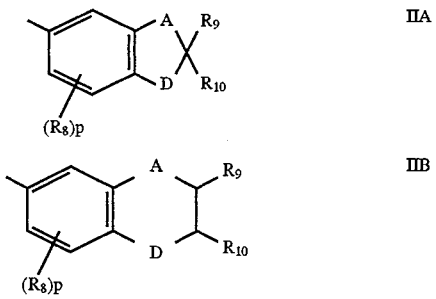

wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_8$ is $C_1$–$C_6$ alkyl, $C_1$–$C_6$ alkoxy, hydroxy, chloro or fluoro; $R_9$ and $R_{10}$ are each hydrogen or $C_1$–$C_6$ alkyl; and p is the integer 0, 1, or 2; (iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$) cycloalkyl, chloro($C_3$–$C_6$)cycloalkyl, and fluoro($C_3$–$C_6$) cycloalkyl; and (v) the group represented by the following graphic formula:

wherein X in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl, and thienyl, each of said group substituents in this part (v) being $C_1$–$C_4$ alkyl, $C_1$–$C_4$ alkoxy, fluoro, or chloro; or (vi) B and B' taken together form fluoren-9-ylidene, mono-, or di-substituted fluoren-9-ylidene or form a member selected from the group consisting of saturated $C_3$–$C_{12}$ spiromonocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated $C_7$–$C_{12}$ spiro-bicyclic hydrocarbon rings, e.g., bicyclo [2.2.1]heptylidene, i.e., norbornylidene, 1,7,7-trimethyl bicyclo[2.2.1]heptylidene, i.e., bornylidene, bicyclo[3.2.1] octylidene, bicyclo[3.3.1]nonan-9-ylidene, bicyclo[4.3.2] undecane, and saturated $C_7$–$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$] dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, and benzothien-2-yl, each of said phenyl and aromatic heterocyclic substituents being selected from the group consisting of hydroxy, amino, mono($C_1$–$C_3$) alkylamino, di($C_1$–$C_3$)alkylamino, piperidino, morpholino, pyrryl, $C_1$–$C_3$alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIA and IIB, wherein A is carbon and D is oxygen, $R_8$ is $C_1$–$C_3$ alkyl or $C_1$–$C_3$ alkoxy, $R_9$ and $R_{10}$ are each hydrogen or $C_1$–$C_4$ alkyl; and p is the integer 0 or 1; (iv) $C_1$–$C_4$ alkyl; and (v) the group represented by the graphic formula IIC wherein X is hydrogen or methyl and Z is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, and benzothien-2-yl, each of said phenyl and aromatic heterocyclic substituents being selected from the group consisting of hydroxy, $C_1$–$C_3$ alkyl, $C_1$–$C_3$ alkoxy, fluoro and chloro; and (iii) the group represented by graphic formula IIA, wherein A is carbon and D is oxygen, $R_8$ is $C_1$–$C_3$ alkyl or $C_1$–$C_3$ alkoxy, $R_9$ and $R_{10}$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

Compounds represented by graphic formula I having the substituents $R_3$, $R_4$, B, and B', described hereinbefore, may be prepared by the following Reactions A through E. Methods for the preparation of compounds represented by graphic formula I including the substituents $R_1$ and $R_2$, described hereinbefore, are included in Reactions D and E. Compounds represented by graphic formula V, VA, or VB are either purchased or prepared by Friedel—Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel—Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B or VB in Reaction C). R and R' represent possible substituents, as described hereinbefore with respect to graphic formula I.

Reaction A

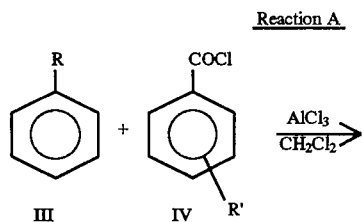

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

Reaction B

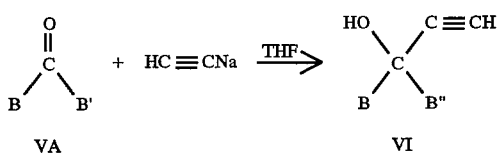

In Reaction C, a substituted or unsubstituted benzophenone represented by graphic formula VB is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. If $R_3$ and $R_4$ on the benzophenone are not identical, i.e., not structurally symmetrical, a mixture of cis and trans half esters will be formed that will require further purification to isolate a distinct isomer. The half ester (VIII) undergoes cyclodehydration in the presence of acetic anhydride to form the acetoxynaphthalene represented by graphic formula IX. This product is hydrolyzed in an aqueous alcoholic solution of base, such as sodium hydroxide, followed by treatment with aqueous hydrochloric acid ($H^+$) to form the carboxynaphthol represented by graphic formula X.

Reaction C

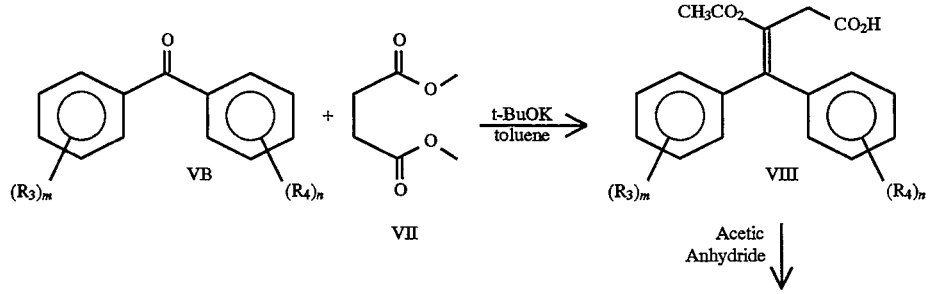

-continued
Reaction C

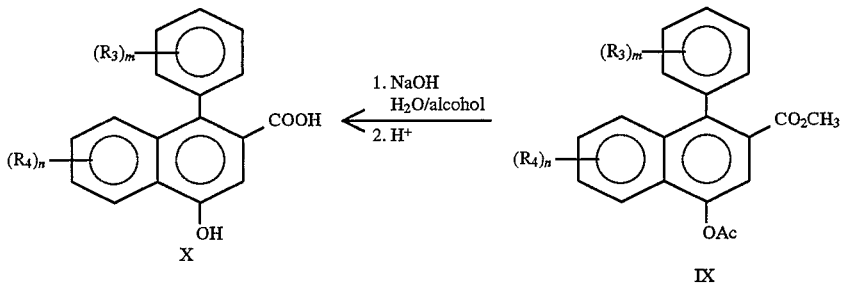

In Reaction D, the carboxynaphthol represented by graphic formula X is cyclized by heating, e.g., from about to about 220° C., in the presence of an acid, such as phosphoric acid, to a hydroxy-substituted benz-fused fluorenone represented by graphic formula XI. See the article by F. G. Baddar et al, in the J. Chem. Soc., page 986, 1958. An alternate method of synthesizing the compound represented by graphic formula XI is described by C. F. Koelsch in the Journal of Organic Chemistry, volume 26, page 2590, 1961.

Coupling of the compound represented by graphic formula XI with a propargyl alcohol represented by graphic formula VI in the presence of a catalytic amount of an acid, e.g., dodecylbenzene sulfonic acid (DBSA), results in the indeno-fused naphthopyran represented by graphic formula IA. The reduction of the compound represented by graphic formula XI via the Wolff-Kishner reduction results in the compound represented by graphic formula XIA. Coupling of the compound represented by graphic formula XIA with a propargyl alcohol represented by graphic formula VI results in the indeno-fused naphthopyran represented by graphic formula IB. The replacement of the hydrogens in graphic formula IB by alkyl groups, e.g., $R_1$ and $R_2$, is accomplished by reaction of the compound IB with trialkyl aluminum to produce the compound represented by graphic formula IC.

Compounds similar to the compounds represented by graphic formula IC in which $R_1$ and $R_2$ are alkoxy instead of alkyl or $R_1$ and $R_2$ are taken together to form a spiro-heterocyclic group containing 2 oxygen atoms and 3 to 6 carbon atoms including the spirocarbon atom may be prepared by reacting the compound represented by graphic formula IA with an alcohol or a diol, respectively, in the presence of a catalytic amount of acid.

Reaction D

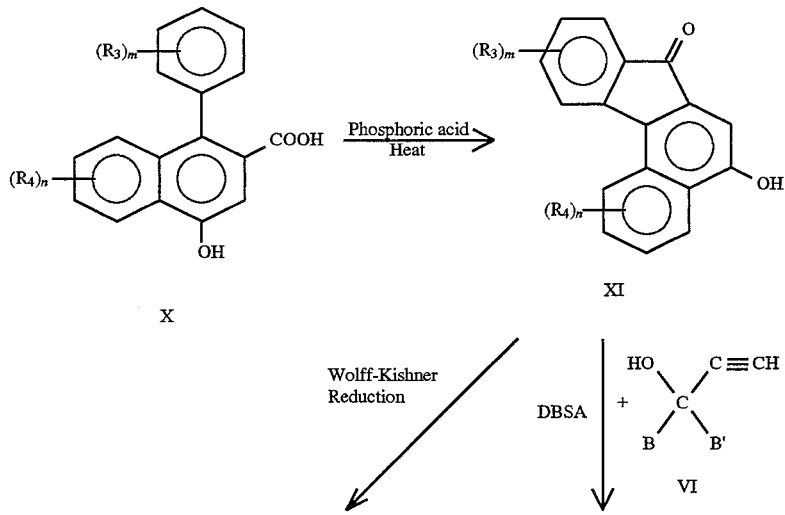

-continued
Reaction D

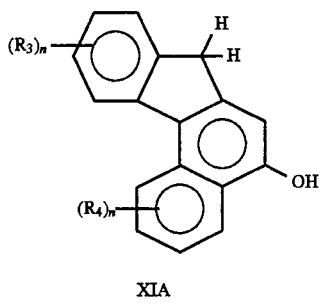 XIA

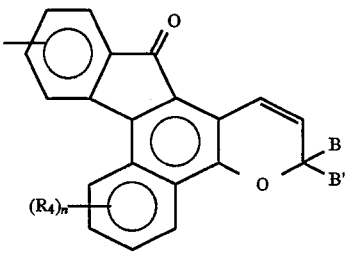 IA

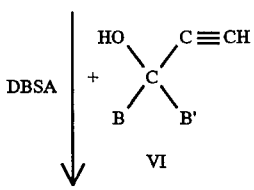 VI

DBSA

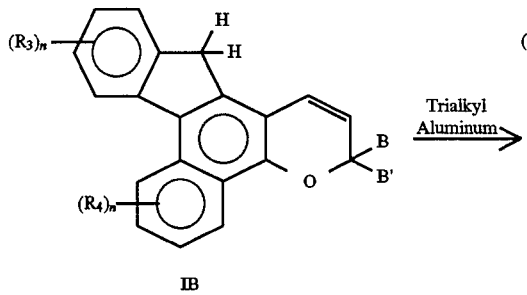 IB

Trialkyl Aluminum →

IC

In Reaction E, further methods for preparing compounds represented by graphic formula I having different $R_1$ and $R_2$ substituents are described. Starting with the compound represented by graphic formula IA, reduction with lithium aluminum hydroxide (LAH) results in the compound represented by graphic formula ID. Other methods for reducing the carbonyl group are described in the text *The Chemistry of the Carbonyl Group*, Chapter 11, Saul Patai, Editor, 1966, Interscience Publishers.

The reaction of the compound represented by graphic formula ID with an acyl chloride having the potential substituent R' results in the compound represented by graphic formula IE. Another pathway for incorporating different $R_1$ and $R_2$ substituents on the compound represented by graphic formula IA is by reacting the compound (IA) with a Grignard or lithium reagent having the potential substituent R to produce the compound represented by graphic formula IF. Subsequent reaction of the compound represented by graphic formula IF with an alcohol having the potential substituent R' in the presence of an acid such as hydrochloric acid results in the compound represented by graphic formula IG.

Reaction E

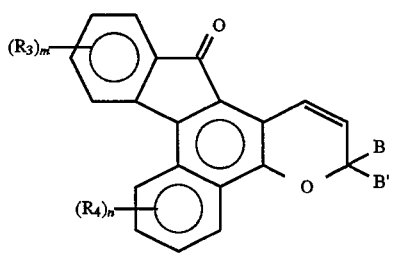

IA

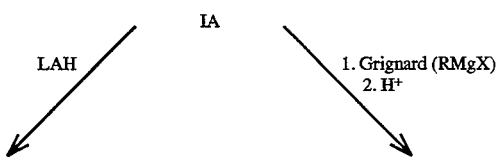

LAH

1. Grignard (RMgX)
2. $H^+$

-continued
Reaction E

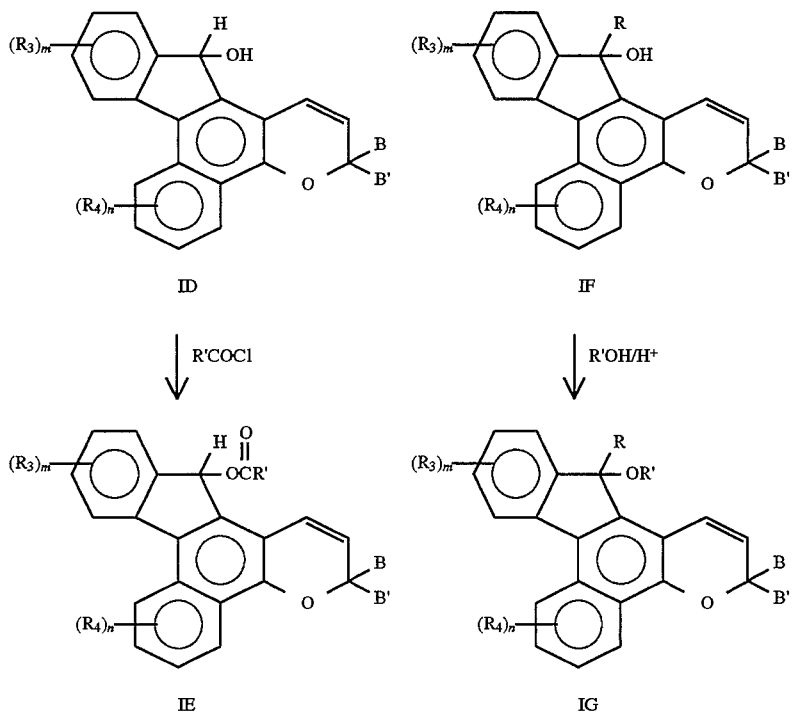

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from orange to blue/gray.

Examples of contemplated naphthopyran compounds within the scope of the invention are the following:

(a) 3-(4-methoxyphenyl)-3-(3-methyl-4-methoxyphenyl)-13-hydroxy-indeno[2,1-f]naphtho[1,2-b]pyran;

(b) 3,3-di(4-methoxyphenyl)-13-hydroxy-13-methyl-indeno[2,1-f]naphtho[1,2-b]pyran;

(c) 3-(4-methoxyphenyl)-3-(2,3-dihydrobenzofur-5-yl)-13-hydroxy-13-methyl-indeno[2,1-f]naphtho[1,2-b]pyran;

(d) 3-(4-methoxyphenyl)-3-(2,3-dihydrobenzofur-5-yl)-13-acetoxy-6,11-dimethoxy-13-methyl-indeno[2,1-f]naphtho[1,2-b]pyran;

(e) 3,3-di(4-methoxyphenyl)-6,11-dimethyl-13-methoxy-indeno[2,1-f]naphtho[1,2-b]pyran;

(f) 3,3-di(4-methoxyphenyl)-6-methyl-11-fluoro-13,13-diethoxy-indeno[2, 1-f]naphtho[1,2-b]pyran;

(g) 3,3-di(4-methoxyphenyl)-6,11-dimethyl-13-(1-methylethyl)-13-hydroxy-indeno[2,1-f]naphtho[1,2-b]pyran;

(h) 3-(4-methoxyphenyl)-3-(3,4-dimethoxyphenyl)-6,11-dimethyl-13,13-dipropyl-indeno[2,1-f]naphtho[1,2-b]pyran; and (i) 3,3-di(4-methoxyphenyl)-6,11-dimethyl-13-butyl-13-hydroxy-indeno[2,1-f]naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline) pyridobenzoxazines, spiro(benzindoline) pyridobenzoxazines, spiro(benzindoline)naphthoxazines, spiro(indoline)benzoxazines, and mixtures of such photochromic compounds.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400-550 nanometer range is moderately larger than in the 550-700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., x=X/(X+Y+Z) and y=Y/(X+Y+Z). Color as described in the CIE system can be plotted on a chromaticity diagram, usually a plot of the chromaticity coordinates x and y. See pages 47–52 of *Principles of Color Technology*; by F. W. Billmeyer, Jr., and Max Saltzman, Second Edition, John Wiley and Sons, New York (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol(allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80-90 percent diethylene glycol bis (allyl carbonate) and 10-20 percent vinyl acetate, particularly 80-85 percent of the bis(allyl carbonate) and 15-20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE 1

STEP 1

Potassium t-butoxide (75 grams, 0.67 mole) was added to a reaction flask containing 200 milliliters (mL) of toluene. The reaction flask was equiped with an overhead stirrer, dropping funnel, and a condenser with nitrogen inlet. The contents of the reaction flask was heated to reflux temperature and a mixture of benzophenone (91 grams, 0.5 mole), dimethyl succinate (90 grams, 0.62 mole), and toluene (100 grams) was added over a period of one-half hour. The resulting pasty mixture was refluxed an additional two hours, cooled, and about 400 mL of water was added and mixed well. The aqueous layer was separated, acidified with dilute hydrochloric acid, and extracted with 200 mL of toluene. The solvents, toluene and residual t-butanol, were removed on the rotary evaporator to produce a near quantitative yield of crude half-ester, 4,4-diphenyl-3-methoxycarbonyl-3-butenoic acids. This material was not purified further but was used directly in the next step.

STEP 2

The crude half-ester from Step 1 was added to a reaction flask containing 200 mL of toluene. Acetic anhydride (100 grams) and anhydrous sodium acetate (15 grams) were added and the mixture was refluxed for 17 hours. The mixture was cooled and the solvent, toluene, was removed on a rotary evaporator. The resulting residue was dissolved in 200 mL of methylene chloride and stirred. Water (200 mL) was added followed by the slow addition of solid sodium carbonate until carbon dioxide evolution ceased. The methylene chloride layer was separated and washed with water. The solvent, methylene chloride, was removed on a rotary evaporator to yield a viscous oil, containing primarily 1-phenyl-2-methoxycarbonyl-4-acetoxy-naphthalene. This material was not purified further but was used directly in the next step.

STEP 3

The oil containing 1-phenyl-2-methoxycarbonyl-4-acetoxy-naphthalene from Step 2 was added to a reaction flask containing 400 mL of methanol. Two mL of concentrated hydrochloric acid was added and the mixture was heated to reflux. After approximately four hours, the volume of the mixture was reduced by half on a rotary evaporator. As the mixture cooled, the product started to crystallize. The resulting crystals were suction filtered, washed with fresh methanol, and dried. The recovered product, 100 grams, had a melting point of 174°–176° C. and a nuclear magnetic resonance spectrum (NMR) showing the product to have a structure consistent with 4-phenyl-3-methoxycarbonyl-1-naphthol.

STEP 4

The 4-phenyl-3-methoxycarbonyl-1-naphthol, 100 grams, from Step 3, was added to a reaction flask containing 350 mL of a 10 weight percent aqueous sodium hydroxide solution and 50 mL of methanol. The mixture was refluxed for one hour, cooled, then slowly poured into a beaker containing approximately one liter of cold (approx. 4° C.) dilute hydrochloric acid. About 90 grams of the resulting crystalline product, 1-phenyl-4-hydroxy-2-naphthoic acid, having a melting point of 210°–212° C., was collected by vacuum filtration.

STEP 5

Thirty five grams of 1-phenyl-4-hydroxy-2-naphthoic acid, from Step 4, was added to a reaction flask containing 35 grams of a 85 weight percent phosphoric acid solution. The resulting mixture was heated to 190°–200° C. and kept at this temperature for one hour. During this time a deep red solid product formed. The mixture was cooled and 200 mL of water was added. The solid was broken up with a spatula, filtered, and washed successively with water, 5 weight percent aqueous sodium bicarbonate, and water. Eighteen grams of the red colored product, 5-hydroxy-7H-benzo[C]-fluoren-7-one, were recovered by vacuum filtration.

STEP 6

5-Hydroxy-7H-benzo[C]-fluoren-7-one (6 grams), from Step 5, was added to a reaction flask containing 1,1-di(4-methoxyphenyl)-2-propyn-1-ol (6 grams) and 100 mL of toluene. The resulting mixture was stirred and heated to 50° C., three drops of dodecybenzene sulfonic acid were added, and the reaction mixture was kept at 50° C. for five hours. After the reaction mixture cooled to room temperature, it was filtered and the collected filtrate was washed three times with 5 weight percent aqueous sodium hydroxide. The solvent, toluene, was removed on a rotary evaporator and the desired product crystallized on the addition of acetone to the residue. The solid was vacuum filtered, washed with fresh acetone, and dried to yield 6.2 grams of a red-orange colored product having a melting point of 190°–191° C. An NMR showed the product to have a structure consistent with 3,3-di(4-methoxyphenyl)-13-oxo-indeno[2,1-f]naphtho[1,2-b]pyran.

STEP 7

Three grams of 3,3-di(4-methoxyphenyl)-13-oxo-indeno[2,1-f]naphtho[1,2-b]pyran from Step 6, was added to a reaction flask containing 50 mL of anhydrous diethyl ether. Small portions of lithium aluminum hydride were added to the stirred mixture until all of the red-orange color disappeared. The reaction mixture was stirred an additional ten minutes, quenched with a small amount of ethanol, and poured into 200 mL of 5 weight percent aqueous hydrochloric acid. The organic layer was separated, washed with water, filtered, and the solvent, diethyl ether, was removed on a rotary evaporator. The addition of approximately ten milliliters of a 2:1 mixture of hexane:ethyl acetate to the residue caused the crystallization of the desired product. The recovered crystals were washed with a small amount of a 2:1 mixture of hexane:ethyl acetate and dried to yield 2.6 grams of product having a melting point of 127°–129° C. An NMR spectrum showed the product to have a structure consistent with 3,3-di(4-methoxyphenyl)-13-hydroxy-indeno[2,1-f]naphtho[1,2-b]pyran.

EXAMPLE 2

The process of Example 1 was followed except that in Step 7, three grams of 3,3-di(4-methoxyphenyl)-13-oxo-indeno[2,1-f]naphtho[1,2-b]pyran was added to a reaction flask containing 50 mL of anhydrous tetrahydrofuran. The mixture was cooled in an ice bath and protected from moisture with a nitrogen pad while an excess of methyl Grignard reagent was added to the reaction with stirring. After stirring an additional ten minutes, 200 mL of 5 weight percent aqueous hydrochloric acid was added and the organic layer was separated and washed with water. The solvent, tetrahydrofuran, was removed on a rotary evaporator. The addition of approximately ten milliliters of a 2:1 mixture of hexane:ethyl acetate to the residue caused the crystallization of a non photochromic material. This material was separated by filtration. The filtrate was column chromatographed on silica using a 3:1 mixture of hexane:ethyl acetate as elutant. The desired product, which crystallized from ether, was filtered and dried to yield 0.7 grams of a product having a melting point of 125°–126° C. An NMR spectrum showed the product to have a structure consistent with 3,3-di(4-methoxyphenyl)-3-hydroxy-13-methyl-indeno[2,1-f]naphtho[1,2-b]pyran.

EXAMPLE 3

The process of Example 1 was followed except that in Step 6, 1-(2,3-dihydrobenzofur-5-yl)-1-(4-methoxyphenyl)-2-propyn-1-ol was used in place of 1,1-di(4-methoxyphenyl)-2-propyn-1-ol. The resulting product, 3-(4-methoxyphenyl)-3-(2,3-dihydrobenzofur-5-yl)-13-oxo-indeno[2,1-f]naphtho[1,2-b]pyran was used in place of 3,3-di(4-methoxyphenyl)-13-oxo-indeno[2,1-f]naphtho[1,2-b]pyran in Step 7, as described in Example 2. The resulting diasteriomeric mixture was crystallized from an ether hexane mixture, filtered, and dried. The recovered crystals, 3.7 grams, melted over a temperature range of 121°–135° C. An NMR spectrum showed the product to have a structure consistent with 3-(4-methoxyphenyl)-3-(2,3-dihydrobenzofur-5-yl)-13-hydroxy-13-methyl-indeno[2,1-f]naphtho[1,2-b]pyran.

EXAMPLE 4

The process of Example 1 was followed except that in Step 1, 200 grams of toluene instead of 100 grams was used in solubilizing the 4,4'-dimethylbenzophenone (105 grams, 0.5 mole) which was used in place of benzophenone to produce di(4-methylphenyl)-3-methoxycarbonyl-3-butenoic acid. This Stobbe half ester was used in Step 2 to produce 100 grams of 1-(4-methylphenyl)-2-methoxycarbonyl-4-acetoxy-6-methyl naphthalene, having a melting point of 144°–146° C. Step 3 of the process of Example 1 was ommitted. In Step 4, 1-(4-methylphenyl)-2-methoxycarbonyl-4-acetoxy-6-methyl naphthalene was used in place of 4-phenyl-3-methoxycarbonyl-1-naphthol to produce 1-(4-methylphenyl)-4-hydroxy-6-methyl-2-naphthoic acid, having a melting point of 210°–213° C. In Step 5, 100 grams of this product was used in place of 1-phenyl-4-hydroxy-2-naphthoic acid and mixed with xylene (250 grams) and 250 grams of a 85 weight percent phosphoric acid solution. The stirred mixture was refluxed in a one liter flask equipped with a Dean-Stark trap for 20 hours to produce 90 grams of 3,9-dimethyl-5-hydroxy-7H-benzo[C]-fluoren-7-one, of which 2.0 grams was used in Step 6 with 3.0 grams of 1-(2,3-dihydrobenzofur-5-yl)-1-(4-methoxyphenyl)-2-propyn-1-ol. The resulting product, 3-(4-methoxyphenyl)-3-(2,3-dihydrobenzofur-5-yl)-6,11-dimethyl-13-oxo-indeno[2,1-f]naphtho[1,2-b]pyran, was used in Step 7, as described in Example 2, except that an ether hexane mixture was used to crystallize the product. The recovered product, 1.2 grams, had a melting point of 198°–200° C. An NMR spectrum showed the product to have a structure consistent with 3-(4-methoxyphenyl)-3-(2,3-dihydrobenzofur-5-yl)-13-hydroxy-6,11,13-trimethyl-indeno[2,1-f]naphtho[1,2-b]pyran.

EXAMPLE 5

The process of Example 4 was followed except that in Step 6, 10 grams of 1,1-di(4-methoxyphenyl)-2-propyn-1-ol was reacted with 10 grams of 3,9-dimethyl-5-hydroxy-7H-benzo[C]-fluoren-7-one to produce 16 grams of product having a melting point of 227°–229° C. An NMR spectrum showed the product to have a structure consistent with 3,3-di(4-methoxyphenyl)-6,11-dimethyl-13-oxo-indeno[2,1-f]naphtho[1,2-b]pyran. In Step 7, 10 grams of the pyran product from Step 6 was reacted with an excess of methyl Grignard and the desired product was crystallized from methanol instead of an ether hexane mixture. The recovered product, 8 grams, had a melting point of 233°–235° C. An NMR spectrum showed the product to have a structure consistent with 3,3-di(4-methoxyphenyl)-6,11,13-trimethyl-13-hydroxy-indeno[2,1-f]naphtho[1,2-b]pyran.

EXAMPLE 6

The process of Example 5 was followed except that in Step 7, an excess of ethyl Grignard reagent, in place of methyl Grignard reagent, was reacted with 3 grams of 3,3-di(4-methoxyphenyl)-6,11-dimethyl-13-oxo-indeno[2,1-f]naphtho[1,2-b] pyran to produce 1.4 grams of a crystalline product that had a melting point of 153°–155° C. An NMR spectrum showed the product to have a structure consistent with 3,3-di(4-methoxyphenyl)-6,11-dimethyl-13-ethyl-13-hydroxy-indeno[2,1-f]naphtho[1,2-b]pyran.

EXAMPLE 7

The process of Example 5 was followed except that in Step 7, an excess of isopropyl Grignard reagent, in place of methyl Grignard, was reacted with 3 grams of 3,3-di(4-methoxyphenyl)-6,11-dimethyl-13-oxo-indeno[2,1-f]naphtho[1,2-b]pyran to produce 1.7 grams of a crystalline product that had a melting point of 209°–210° C. An NMR spectrum showed the product to have a structure consistent with 3,3-di(4-methoxyphenyl)-6,11-dimethyl-13-(1-methylethyl)-13-hydroxy-indeno[2,1-f]naphtho[1,2-b]pyran.

EXAMPLE 8

The process of Example 5 was followed except that in Step 7, an excess of t-butyl Grignard reagent, in place of methyl Grignard, was reacted with 3 grams of 3,3-di(4-methoxyphenyl)-6,11-dimethyl-13-oxo-indeno[2,1-f]naphtho[1,2-b]pyran to produce 1.0 gram of a crystalline product that had a melting point of greater than 240° C. An NMR spectrum showed the product to have a structure consistent with 3,3-di(4-methoxyphenyl)-6,11-dimethyl-13-(1,1-dimethylethyl)-13-hydroxy-indeno[2,1-f]naphtho[1,2-b]pyran.

EXAMPLE 9

The process of Example 5 was followed except that in Step 7, an excess of n-butyl lithium reagent, in place of methyl Grignard, was reacted with 3 grams of 3,3-di(4-methoxyphenyl)-6,11-dimethyl-13-oxo-indeno[2,1-f]naphtho[1,2-b]pyran to produce 1.0 gram of a crystalline product that had a melting point of 148°–150° C. An NMR spectrum showed the product to have a structure consistent with 3,3-di(4-methoxyphenyl)-6,11-dimethyl-13-butyl-13-hydroxy-indeno[2,1-f]naphtho[1,2-b]pyran.

COMPARATIVE EXAMPLE 1

4-Phenyl-3-methoxycarbonyl-1-naphthol (2 grams) from Step 3 of Example 1 and 1,1-di(4-methoxyphenyl)-2-propyn-1-ol (2 grams) were added to a reaction flask containing 100 milliliters (mL) of toluene. The resulting mixture was stirred and heated to 40° C., two drops of dodecylbenzene sulfonic acid were added, and the reaction mixture was kept at 40° C. for three hours. After the reaction mixture cooled to room temperature, it was added to an equal volume of water. The organic layer was separated and the solvent, toluene, was removed on a rotary evaporator. The resulting residue was chromatographed on silica using a 2:1 mixture of hexane:ethyl acetate as the eluant. The photochromic fractions were combined, the solvent was evaporated, and the desired product was induced to crystallize from a hexane/diethyl ether mixture. The recovered crystals were dried and filtered to yield 2 grams of product having a melting point of 168°–169° C. An NMR spectrum showed the product to have a structure consistent with 2,2-di(4-methoxyphenyl),5-methoxycarbonyl,6-phenyl-[2H]-naphtho[1,2-b]pyran.

EXAMPLE 10

Part A

Testing was done with selected photochromic naphthopyrans imbibed into test square polymerizates. The test square polymerizates were prepared from a diethylene glycol bis(allyl carbonate) composition sold by PPG Industries, Inc. under the designation CR-307 optical resin and measured ¼ inch (0.6 centimeters)×2 inches (5.1 centimeters)×2 inches (5.1 centimeters). The test squares were imbibed by the following procedure. Each naphthopyran was dissolved to form a 10 weight percent solution in a 1:9 mixture of ethyl cellulose:toluene. The solution was then spin coated onto the test squares and allowed to dry. Samples were then heated in a hot-air oven at 135°–155° C. for a period of time sufficient to thermally transfer the photochromic into the test squares. After cooling, the ethyl cellulose/toluene resin film was removed from the test squares by washing with acetone. The residence time in the oven for the test squares was adjusted to imbibe amounts of the naphthopyran compounds that would yield comparable absorbance values at the lambda max (UV) of the individual compounds.

Part B

The photochromic test squares of Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach the photochromic compounds. The test squares were then cooled to room temperature, exposed to fluorescent room lighting for at least 2 hours and then kept covered for at least 2 hours prior to testing on an optical bench maintained at 75° F. (23.9° C.).

The optical bench comprises a 150 watt Xenon arc lamp, a tungsten lamp, power supplies for both lamps, condensing lenses as needed to maintain collimated light beams from both lamps, a remote controlled shutter, a copper sulfate bath acting as a heat sink for the arc lamp, a Schott WG-320 nm cut-off filter which removes short wavelength radiation, neutral density filter(s), a sample holder in which the sample to be tested is inserted, a photopic filter, light detector, and radiometer assembly, a strip chart recorder, and a means for maintaining the alignment of the aforestated components during testing.

Change in optical density ($\Delta$OD) of a sample was determined by inserting a photochromic test sample in the bleached state into the sample holder, adjusting the transmittance scale to 100%, opening the shutter from the Xenon lamp to provide ultraviolet radiation to change the sample from the bleached state to an activated (darkened) state, measuring the transmittance through the sample. The transmittance was measured by directing a beam of light from the tungsten lamp at a small angle normal to the surface of the sample, through the sample, and to a photopic filter, light detector and radiometer assembly. The photopic filter passes wavelengths such that the detector mimics the response of the human eye and produces output signals that are processed by the radiometer. The change in optical density was calculated according to the formula $\Delta \text{OD} = \log(100/\% \text{Ta})$ where % Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 20 minutes. The lambda max (Vis) is the wavelength in the visible spectrum at which the maximum absorption of the activated (colored) form of the photochromic compound in the test square occurs. The bleach rate (T ½) is the time interval in seconds for the absorbance of the activated form of the naphthopyran in the test squares to reach one half the highest absorbance at room temperature (75° F., 23.9° C.) after removal of the source of activating light. Results for the compounds of the Examples are tabulated in Table 1.

Part C

The principal products of the Example Compounds were dissolved in diethylene glycol dimethyl ether. The concentration of the resulting solutions was approximately 0.5 milligram per milliliter. Each solution was tested in a UV spectrophotometer to determine the wavelength in the ultraviolet range closest to the visible spectrum at which the absorption of the photochromic compound occurs. These results are reported as the lambda($\lambda$) max (UV) in Table 2.

The lambda max (Vis) is the wavelength in the visible spectrum at which the maximum absorption of the activated (colored) form of the photochromic compound in a test square occurs. The lambda max (Vis) wavelengths reported in Table 2 were determined by testing the photochromic test squares polymerizates of Part A on the optical bench of Part B.

The molar absorptivity or molar extinction coefficient (s) reported in Table 2 is equal to the absorbance of the photochromic compound in a diethylene glycol dimethyl ether solution at the λ max in the UV (A) divided by the path length of the spectrophotometer cell (b) multiplied by the concentration of the photochromic compound solution in moles per liter (M) according to the formula: ε=A/bM. The molar absorptivity was measured in a UV spectrophotometer for a $2 \times 10^{-3}$ molar solution of selected Example compounds in a 0.1 centimeter quartz cell.

TABLE 1

| Compound Example | Sensitivity ΔOD/min | ΔOD @ Saturation | Bleach Rate T½ (sec) |
|---|---|---|---|
| 1 | 1.13 | 0.89 | 207 |
| 2 | 1.20 | 0.79 | 119 |
| 3 | 0.89 | 0.77 | 265 |
| 4 | 0.67 | 0.74 | 401 |
| 5 | 0.78 | 0.73 | 362 |
| 6 | 0.72 | 0.64 | 237 |
| 7 | 0.66 | 0.64 | 264 |
| 8 | 0.57 | 0.61 | 313 |
| 9 | 0.73 | 0.65 | 206 |
| CE 1 | 0.49 | 0.38 | 152 |

The data presented in Table 1 show that each tested compound of the present invention, in comparison to Comparative Example (CE) 1, has a higher Δ OD at saturation, i.e., activated intensity, and a higher coloration rate, i.e., sensitivity (ΔOD/min). The Example compounds also demonstrate an acceptable bleach rate, i.e., fade rate.

TABLE 2

| Compound Example | λ max (nm) UV | Molar Absorpt. (ε) | λ max (nm) Vis (minor) | λ max (nm) Vis (major) |
|---|---|---|---|---|
| 1 | 361 | – | 436 | 562 |
| 2 | 359 | 9666 | 435 | 560 |
| 3 | 359 | 9186 | 438 | 570 |
| 4 | 360 | – | 443 | 575 |
| 5 | 359 | 10,165 | 438 | 570 |
| 6 | 360 | – | 439 | 572 |
| 7 | 359 | 9677 | 439 | 577 |
| 8 | 362 | – | 440 | 576 |
| 9 | 359 | 9471 | 439 | 575 |
| CE 1 | 347 | 6174 | 420 | 517 |

The data presented in Table 2 show that each tested compound of the present invention, in comparison to CE 1, has a higher λ max UV and λ max Vis of the major peak which demonstrates a bathochromic shift in the UV and visible spectra, and a higher molar absorptivity or molar coefficient of extinction (ε) in the UV spectrum.

The present invention has been described with reference to specific details of particular embodiments thereof. It is not intended that such details be regarded as limitations upon the scope of the invention except insofar as to the extent that they are included in the accompanying claims.

I claim:

1. A naphthopyran compound represented by the following graphic formula:

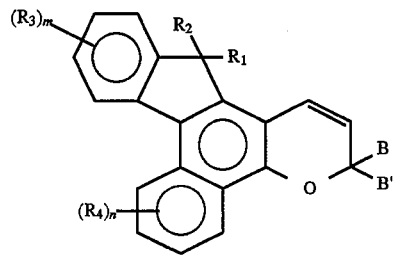

wherein, (a) $R_1$ and $R_2$ together form an oxo group, a spiro heterocyclic group having 2 oxygen atoms and from 3 to 6 carbon atoms including the spirocarbon atom, or $R_1$ and $R_2$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group, —C(O)W, wherein W is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$) alkylamino, or $R_1$ and $R_2$ are each the group, —OR$_5$, wherein $R_5$ is $C_1$–$C_6$ alkyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$) alkyl substituted $C_3$–$C_7$ cycloalkyl, $C_1$–$C_6$ chloroalkyl, $C_1$–$C_6$ fluoroalkyl, allyl, the group, —CH(R$_6$)X, wherein $R_6$ is hydrogen or $C_1$–$C_3$ alkyl and X is CN, CF$_3$, or COOR$_7$, and $R_7$ is hydrogen or $C_1$–$C_3$ alkyl, or $R_5$ is the group, —C(O)Y, wherein Y is hydrogen, $C_1$–$C_6$ alkyl, $C_1$–$C_6$ alkoxy, the unsubstituted, mono- or di-substituted aryl groups phenyl or naphthyl, phenoxy, mono- or di-($C_1$–$C_6$)alkyl substituted phenoxy, mono- or di-($C_1$–$C_6$)alkoxy substituted phenoxy, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$) alkoxy substituted phenylamino, each of said phenyl, benzyl and aryl group substituents being $C_1$–$C_6$ alkyl or $C_1$–$C_6$ alkoxy;

(b) $R_3$ and $R_4$ are each $C_1$–$C_6$ alkyl, $C_1$–$C_6$ alkoxy, chloro, or fluoro, and m and n are each the integers 0, 1, or 2;

(c) B and B' are each selected from the group consisting of:

(i) the unsubstituted, mono-, di-, and tri-substituted aryl groups, phenyl and naphthyl;

(ii) the unsubstituted, mono-, and di-substituted aromatic heterocyclic groups pyridyl, furanyl, benzofuran-2-yl, benzofuran-3-yl, thienyl, benzothien-2-yl, benzothien-3-yl, said aryl and aromatic heterocyclic substituents in (c)(i) and (ii) being selected from the group consisting of hydroxy, amino, mono($C_1$–$C_6$)alkylamino, di($C_1$–$C_6$) alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, chloro and fluoro;

(iii) the groups represented by the following graphic formulae:

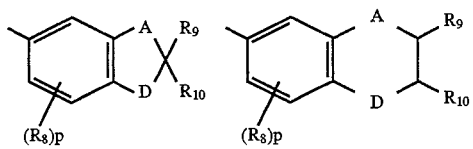

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_8$ is $C_1$–$C_6$ alkyl, $C_1$–$C_6$ alkoxy, hydroxy, chloro or fluoro; $R_9$ and $R_{10}$ are each hydrogen or $C_1$–$C_6$ alkyl; and p is the integer 0, 1, or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)cycloalkyl, chloro($C_3$–$C_6$)cycloalkyl and fluoro($C_3$–$C_6$)cycloalkyl; and (v) the group represented by the following graphic formula:

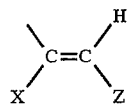

wherein X is hydrogen or $C_1$–$C_4$ alkyl and Z is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, fluoro, or chloro; or (vi) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein, (a) $R_1$ and $R_2$ are each selected from the group consisting of hydrogen, hydroxy, $C_1$–$C_4$ alkyl, $C_3$–$C_6$ cycloalkyl, chloro, fluoro and the group, —$OR_5$, wherein $R_5$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl, the group, —CH($R_6$)X, wherein $R_6$ is hydrogen or $C_1$–$C_2$ alkyl and X is CN or $COOR_7$, and $R_7$ is hydrogen or $C_1$–$C_2$ alkyl, or $R_5$ is the group, —C(O)Y, wherein Y is hydrogen, $C_1$–$C_3$ alkyl, $C_1$–$C_3$ alkoxy, phenyl, naphthyl, mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and said aryl substituents being $C_1$–$C_3$ alkyl or $C_1$–$C_3$ alkoxy;

(b) $R_3$ and $R_4$ are each $C_1$–$C_3$ alkyl, $C_1$–$C_3$ alkoxy, or fluoro, and m and n are each the integers 0 or 1;

(c) B and B' are each selected from the group consisting of:

(i) phenyl, mono-substituted phenyl, and di-substituted phenyl;

(ii) the unsubstituted, mono-, and di-substituted aromatic heterocyclic groups furanyl, benzofuran-2-yl, thienyl, and benzothien-2-yl, said phenyl and aromatic heterocyclic substituents in (c)(i) and (ii) being selected from the group consisting of hydroxy, amino, mono($C_1$–$C_3$)alkylamino, di($C_1$–$C_3$) alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;

(iii) the groups represented by the following graphic formulae:

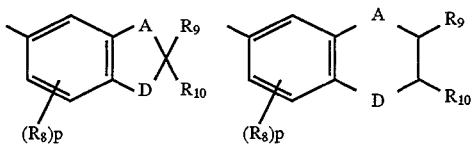

wherein A is carbon and D is oxygen, $R_8$ is $C_1$–$C_3$ alkyl or $C_1$–$C_3$ alkoxy, $R_9$ and $R_{10}$ are each hydrogen or $C_1$–$C_4$ alkyl; and p is the integer 0 or 1;

(iv) $C_1$–$C_4$ alkyl; and (v) the group represented by the following graphic formula:

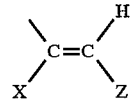

wherein X is hydrogen or methyl and Z is phenyl or mono-substituted phenyl, said phenyl substituent being selected from the group consisting of $C_1$–$C_3$ alkyl, $C_1$–$C_3$ alkoxy, and fluoro; or (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, each of said fluoren-9-xylidene substituents being selected from the group consisting of $C_1$–$C_3$ alkyl, $C_1$–$C_3$ alkoxy, fluoro and chloro.

3. The naphthopyran compound of claim 2 wherein, $R_1$ and $R_2$ are each hydrogen, hydroxy, $C_1$–$C_4$ alkyl, or the group, —$OR_5$, wherein $R_5$ is $C_1$–$C_3$ alkyl; $R_3$ and $R_4$ are each $C_1$–$C_3$ alkyl or $C_1$–$C_3$ alkoxy, and m and n are each the integers 0 or 1; and B and B' are each selected from the group consisting of phenyl, mono-, and di-substituted phenyl, unsubstituted, mono-, and di-substituted aromatic heterocyclic groups furanyl, benzofuran-2-yl, thienyl, and benzothien-2-yl, each of said phenyl and aromatic heterocyclic substituents being selected from the group consisting of hydroxy, $C_1$–$C_3$ alkyl, $C_1$–$C_3$ alkoxy, fluoro and chloro; and the group represented by the following graphic formula:

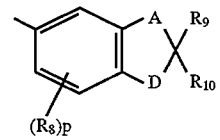

wherein A is carbon and D is oxygen, $R_8$ is $C_1$–$C_3$ alkyl or $C_1$–$C_3$ alkoxy, $R_9$ and $R_{10}$ are each hydrogen or $C_1$–$C_3$ alkyl, and p is the integer 0 or 1; or B and B' taken together form fluoren-9-ylidene, adamantylidene, bornylidene, norbornylidene, or bicyclo(3.3.1)nonan-9-ylidene.

4. A naphthopyran compound selected from the group consisting of:
(a) 3-(4-methoxyphenyl)-3-(3-methyl-4-methoxyphenyl)-13-hydroxy-indeno[2,1-f]naphtho[1,2-b]pyran;
(b) 3,3-di(4-methoxyphenyl)-13-hydroxy-13-methyl-indeno[2,1-f]naphtho[1,2-b]pyran;
(c) 3-(4-methoxyphenyl)-3-(2,3-dihydrobenzofur-5-yl)-13-hydroxy-13-methyl-indeno[2,1-f]naphtho[1,2-b]pyran;
(d) 3-(4-methoxyphenyl)-3-(2,3-dihydrobenzofur-5-yl)-13-acetoxy-6,11-dimethoxy-13-methyl-indeno[2,1-f]naphtho[1,2-b]pyran;
(e) 3,3-di(4-methoxyphenyl)-6,11-dimethyl-13-methoxy-indeno[2,1-f]naphtho[1,2-b]pyran;
(f) 3,3-di(4-methoxyphenyl)-6-methyl-11-fluoro-13,13-diethoxy-indeno[2,1-f]naphtho[1,2-b]pyran;
(g) 3,3-di(4-methoxyphenyl)-6,11-dimethyl-13-(1-methylethyl)-13-hydroxy-indeno[2,1-f]naphtho[1,2-b]pyran;
(h) 3-(4-methoxyphenyl)-3-(3,4-dimethoxyphenyl)-6,11-dimethyl-13,13-dipropyl-indeno[2,1-f]naphtho[1,2-b]pyran; and
(i) 3,3-di(4-methoxyphenyl)-6,11-dimethyl-13-butyl-13-hydroxy-indeno[2,1-f]naphtho[1,2-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance(s) is incorporated or applied.

9. The photochromic article of claim 8 wherein the article is a lens.

10. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance (s) is incorporate or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 2, and (b) at least one other organic photochromic compound having at least one activated absorption maxima within the range of between about 400 and 700 nanometers.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *